US00PP10714P

United States Patent [19]

Nicolai

[11] Patent Number: Plant 10,714

[45] Date of Patent: Dec. 8, 1998

[54] APPLE TREE NAMED 'M9-RN29'

[75] Inventor: René Nicolai, Alken, Belgium

[73] Assignee: Rene Nicolai N.V. Fruitboomwekerij, Belgium

[21] Appl. No.: 991,456

[22] Filed: Dec. 15, 1992

Related U.S. Application Data

[63] Continuation of Ser. No. 642,992, Jan. 18, 1991, abandoned.

[51] Int. Cl.[6] ..... A01H 5/00

[52] U.S. Cl. ..... Plt./34.1

[58] Field of Search ..... Plt./34.1, 35.1, Plt./35.2

[56] References Cited

PUBLICATIONS

Gilles, G.L., et al. "Clonal Selection of M9Apple Rootstock and Influence of Viruses on Homological Value" (Citation; information not provided by applicant in parent application.).

R. Ziebig, et al. "1992 Activity Program for the Agriculture and Forestry Experimental Center" Division VI Agriculture and Forestry, Autonomous Province, Bozen, South Tyrol., 3 pages.

van Oosten, H.J., et al., "Verschillen tussen herkomstin van M9" *De. Fruittielt* n. 32, 1984, pp. 924–926, 950–951, 968–969 and 988–989.

Masseron, A. "Etude et sélection du Paradis Jaune de Metz, porte–greffe du pommier" (Citation information not provided with copies in parent application).

Anon. *Stark Bro's Fruit Free Catalog. & Guide for the Professional Groiver* 1989, Stark Bros Nursery and Orchards Co., Louisana, MO. pp. 18 and 19.

Anon. *Oregon Rootstock, Inc. Catalog,* 1985, Oregon Rootstock, Inc. Woodburn, Oregon pp. 8–15.

Fukey, H.B., "7 Dwarfing Rootstocks for Apple" *Dwarfed Fruit Trees* The Macmillan Co., New York 1964 pp. 123–154.

*Primary Examiner*—Howard J. Locker

*Attorney, Agent, or Firm*—Chernoff, Vilhauer, McClung & Stenzel, LLP

[57] ABSTRACT

This invention relates to a new and distinct apple tree rootstock clone which is useful as a size controlling rootstock. The new clone originated as a mutation of Malling 9 (M9), an unpatented dwarfing apple rootstock. Standard growing apple cultivars propagated on this new rootstock are approximately 65% of the size of like apple trees growing on seedling rootstocks. Compared to its M9 parent, this new clone produces many more and larger lateral branches, has more sharply serrated leaves which are more pale yellow-green in color. The clone is also more vigorous and produces a large number of rooted plants in a given area of stoolbed.

7 Drawing Sheets

This is a continuation of application Ser. No. 07/642,992 filed on Jan. 18, 1991 (now Abandoned).

BACKGROUND AND SUMMARY OF THE INVENTION

The inventor of the subject plant, Rene Nicolai, was the owner of Rene Nicolai Nursery, which propagated and sold Malling Nine (M9) apple tree rootstock. Rootstock are propagated by placing plants in a stoolbed which encourages root growth and then dividing the resulting roots into individual plants. Over the years Mr. Nicolai searched the M9 stoolbeds for M9 mutants which were superior to the parent variety in those characteristics which are desirable for apple tree rootstock.

The subject clone was selected in 1967 from a large stoolbed of M9 plants that was planted in 1960 at the Rene Nicolai Nursery at Linderstroot, 22-B-3820 Alken, Belgium. The original source of the plants in the bed was the East Malling Research Station in England. Following its selection, the clone was assigned a number (RN29) and was propagated for further testing and evaluation.

Since all original M9 rootstocks have been found to be virus infected, RN29 stocks were subsequently heat-treated by application of dry heat in order to obtain virus-free specimens. After heat treatment and subsequent virus testing, the new rootstock clone was again exposed to multiplication techniques (stooling) followed by continued testing and evaluation.

Virus-free RN29 progeny plants were expanded into small stoolbed plantings at several locations which were planted separately in order to examine the new variety's individual characteristics in small semicommercial stoolbed sites. Since 1974 nearly 40,000 plants of the subject variety have been planted at the following six sites and, in the process, many generations of the tree have been produced:

1. A site at Deveaux, Belgium was planted in the spring of 1974 with 1,875 plants of the subject clone.

2. A site at Bordeaux, France was planted in 1977 with 200 plants of the subject clone.

3. A site at Wissenhoeve, Belgium was planted in the spring of 1980 with 7,644 plants of the subject clone.

4. A site near St. Truiden, Belgium was planted in the spring of 1982 with 100 plants of the subject clone.

5. A site at Henkaenrts, Belgium was planted in the spring of 1986 with 3,250 plants of the subject clone.

6. A site at Ephrata, Washington was planted in the spring of 1990 with 26,000 plants of the subject clone.

Clone RN29 was subsequently finally selected as a rootstock clone that continues to possess growth and rooting characteristics that are distinctly different from its M9 parent.

It distinguished itself in these beds from its M9 parent in the following ways:

1. The subject clone produces many more lateral limbs (feathers) than its M9 parent and grows more robustly in the stoolbed (FIGS. 2 and 3, Charts 1 and 2). Average increases in height of the plants in the stoolbed for the RN29 is almost 30% more than for the M9 (FIG. 6, M9; FIG. 7, RN29) and the average increase in the numbers of feathers produced is more than three-fold. There also occurs a great difference in the average length of the individual feathers produced (Chart 2). Because of the more robust growth and increased number of limbs produced by the RN29, a two-fold difference also occurs in the number of leaves produced per stoolbed plant (Chart 2). The number of nodes/shoot and the aver- age individual stem circumference were also greater for RN29 due to its more robust growth habit. Leaf size (adding the length and width together) and the length of the petioles were consistently smaller than the virus-free M9 (Chart 3).

CHART 1

Percent of Layer Plants with Side Limbs (Feathers)
(Test Stooling Beds at Bordeaux, France)

| | Year | | | | |
|---|---|---|---|---|---|
| Rootstock Clone | 79/80 | 80/81 | 81/82 | 82/83 | Average |
| M9 (virus-free) | 13 | 8 | 25 | 0 | 11.5 |
| RN8 | 8 | 6 | 13 | 0 | 6.8 |
| RN19 | 41 | 32 | 44 | 19 | 34.0 |
| RN29 | 39 | 22 | 35 | 15 | 27.8 |

CHART 2

Growth Characteristics
(Test Stooling Beds at Ephrata, Washington)

| Root-stock Clone | Length of Shoot (cm) | Number of Nodes/ Shoot | Number of Spura/ Shoot | Length of Spur (cm) | Number of Leaves/ Shoots | Circumference of Stem (cm) |
|---|---|---|---|---|---|---|
| H9 | 66.80* | 39.20 | 3.00 | 1.50 | 53.00 | 3.24 |
| RN8 | 62.10 | 42.10 | 1.80 | 1.20 | 57.20 | 3.80 |
| RN19 | 78.20 | 41.00 | 18.60 | 8.60 | 88.30 | 3.51 |
| RN29 | 86.20 | 45.60 | 21.40 | 10.30 | 100.00 | 3.54 |

*All numbers shown are the average of 100 plants selected at random.

CHART 3

Leaf Size and Respective Petiole
Length of Respective Rootstock
(Test Stooling Beds at Bordeaux, France)

| Rootstock Clone | Length, L (mm) | Width, W (mm) | L + W (mm) | Length of Petiole |
|---|---|---|---|---|
| M9 (virus free) | 101.7 | 63.8 | 165.5 | 32.5 |
| RN8 | 98.8 | 73.6 | 172.4 | 34.0 |
| RN19 | 91.4 | 60.0 | 151.4 | 30.8 |
| RN29 | 85.5 | 57.1 | 142.6 | 28.5 |

2. The subject clone has the ability to produce many more rooted daughter plants per mother plant (FIG. 1) and per meter of stoolbed row than its M9 parent (Charts 4, 5 and 6). Data collected at the Deveaux, Belgium test site shows a two-fold increase in rooting ability and in the number of rooted plants harvested (Charts 1 and 2) and at a test site at Bordeaux, France a three-and-one-half-fold increase is demonstrated after five years in the stoolbed (Chart 6).

CHART 4

RN29 Stoolbed Production (Deveaux, Belgium)

No. Mother Plants - 1,875
Length of Bed (m) - 6,215

| | Year | | | | |
|---|---|---|---|---|---|
| Grade (mm) | 82/83 | 83/84 | 84/85 | 85/86 | 86/87 |
| 10/12 | 1,700 | 900 | 1,450 | 3,050 | 2,500 |
| 8/10 | 0 | 0 | 2,100 | 0 | 0 |
| 6/10 | 20,600 | 16,400 | 0 | 0 | 13,850 |
| 6/8 | 0 | 0 | 13,040 | 13,500 | 0 |
| 5/7 | 0 | 0 | 0 | 0 | 0 |
| 4/6 | 11,400 | 11,200 | 17,200 | 11,400 | 20,100 |
| 04 | 0 | 3,100 | 0 | 4,900 | 1,050 |
| #2s | 4,500 | 3,900 | 4,000 | 4,400 | 7,900 |
| Totals | 38,200 | 35,500 | 37,790 | 37,250 | 45,400 |
| Per Mother Plant | 20.37 | 18.93 | 20.15 | 19.87 | 24.21 |
| Per Meter | 61.12 | 56.80 | 60.46 | 59.60 | 72.64 |

| | Year | | | | |
|---|---|---|---|---|---|
| Grade (mm) | 87/88 | 88/89 | 89/90 | 90/91 | |
| 10/12 | 2,100 | 0 | 1,200 | 1,650 | |
| 8/10 | 5,150 | 7,050 | 6,050 | 0 | |
| 6/10 | 0 | 0 | 0 | 20,900 | |
| 6/8 | 14,200 | 15,200 | 13,800 | 0 | |
| 5/7 | 0 | 0 | 0 | 0 | |
| 4/6 | 1,400 | 14,500 | 15,900 | 14,100 | |
| 04 | 0 | 0 | 0 | 0 | |
| #2s | 7,500 | 4,300 | 10,800 | 4,700 | |
| | | | | | Average |
| Totals | 30,350 | 41,050 | 47,750 | 41,350 | 82/91 |
| Per Mother Plant | 16.19 | 21.89 | 25.47 | 22.05 | 21.02 |
| Per Meter | 48.56 | 65.68 | 76.40 | 66.16 | 63.05 |

CHART 5

M9(Virus-Free) Stoolbed Production (Deveaux, Belgium)

No. Mother Plants - 561
Length of Bed (m) - 187

| | Year | | | | |
|---|---|---|---|---|---|
| Grade (mm) | 82/83 | 83/84 | 84/85 | 85/86 | 86/87 |
| 10/12 | 225 | 100 | 250 | 750 | 464 |
| 8/10 | 0 | 0 | 450 | 0 | 0 |
| 6/10 | 4,150 | 2,950 | 0 | 2,350 | 2,200 |
| 6/8 | 0 | 0 | 3,400 | 0 | 0 |
| 5/7 | 0 | 0 | 0 | 0 | 0 |
| 4/6 | 1,800 | 1,600 | 2,200 | 1,600 | 3,000 |
| 04 | 0 | 300 | 0 | 0 | 0 |
| #2s | 700 | 800 | 500 | 500 | 1,400 |
| Totals | 6,875 | 5,750 | 6,800 | 5,200 | 7,064 |
| Per Mother Plant | 12.25 | 10.25 | 12.12 | 9.27 | 12.59 |
| Per Meter | 36.76 | 30.75 | 36.36 | 27.81 | 37.78 |

| | Year | | | |
|---|---|---|---|---|
| Grade (mm) | 87/88 | 88/89 | 89/90 | 90/91 |
| 10/12 | 75 | — | — | — |
| 8/10 | 450 | — | — | — |
| 6/10 | 0 | — | — | — |
| 6/8 | 2,700 | — | — | — |
| 5/7 | 0 | — | — | — |
| 4/6 | 2,200 | — | — | — |
| 04 | 0 | — | — | — |
| #2s | 400 | — | — | — |

CHART 5-continued

| M9(Virus-Free) Stoolbed Production (Deveaux, Belgium) | | | | | |
|---|---|---|---|---|---|
| | | | | | Average |
| Totals | 5,825 | — | — | — | 82/91 |
| Per Mother Plant | 10.38 | — | — | — | 11.14 |
| Per Meter | 31.15 | — | — | — | 33.43 |

CHART 6

Average Number of Plants Per Stoolbed Mother Plant (Test Stooling Beds at Bordeaux, France)

| | Year Planted and Age | | | | |
|---|---|---|---|---|---|
| Rootstock Clone | 79/80 2-Yr | 80/81 3-Yr | 81/82 4-Yr | 82/83 5-Yr | Average |
| M9 (virus-free) | 1.2 | 2.6 | .5 | 4.0 | 8.3 |
| RN8 | 2.1 | 3.9 | 3.8 | 6.4 | 16.2 |
| RN19 | 2.6 | 4.4 | 6.5 | 9.1 | 22.6 |
| RN29 | 4.4 | 5.6 | 5.7 | 11.3 | 27.0 |

3. Small differences in leaf color and structure have also been noticed. Leaf color of the subject clone is a pale yellow-green as compared to M9's darker green color (FIG. 5) RN29 is also characterized with leaves which exhibit smaller and sharper serrations than does its M9 parent (FIG. 4).

4. The lack of blooming characteristics of RN29 is very pronounced and in this respect differs distinctly from its M9 parent. The lack of any bloom produced on RN29 two-year-old line-out stocks was contrasted with the amount exhibited by the M9 parent (chart 7).

CHART 7

Bloom Characteristics (Research Station at Gorsum, Belgium - 1985)

| Rootstock Clone | % of Rootstocks With Bloom (1 Year From Stoolbed) |
|---|---|
| RN8 | 29 |
| RN19 | 4 |
| RN29 | 0 |
| M9 (virus-free) | 15 |

DESCRIPTION OF VEGETATIVE CHARACTERISTICS

Figure 1:
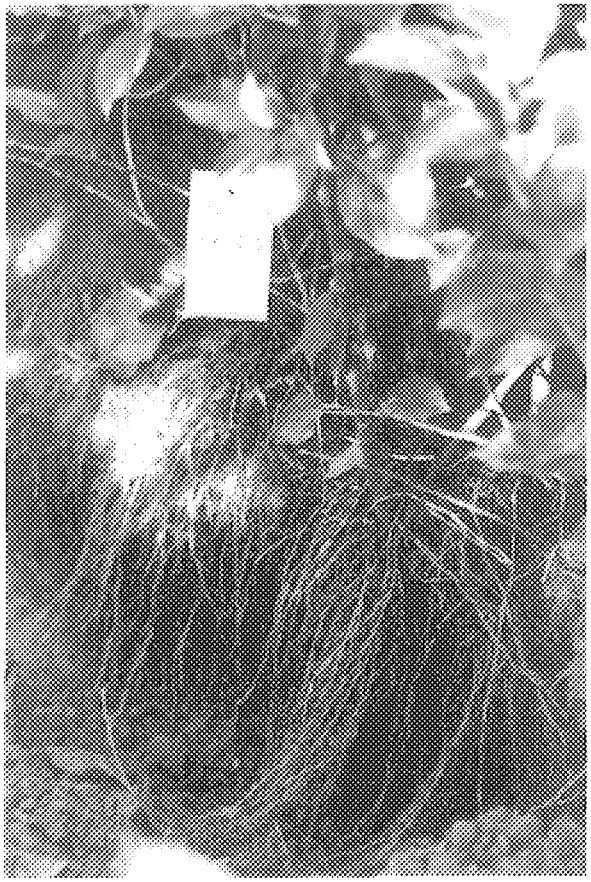
FIG. 1 shows typical root growth following one season in the stoolbed.
Figure 2:
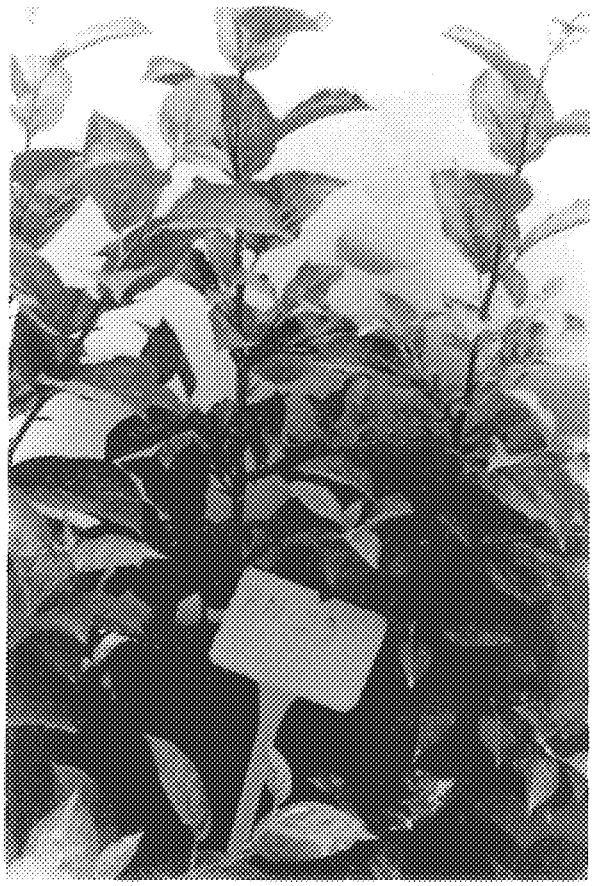
FIG. 2 shows numerous lateral branches and pale yellow-green color of leaves on new shoots.
Figure 3:
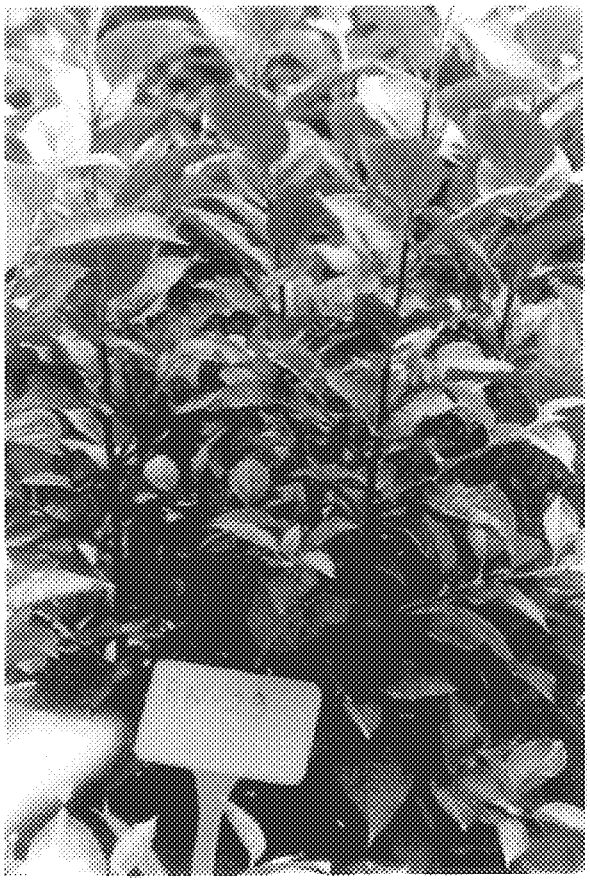
FIG. 3 shows numerous lateral branches (feathers).
Figure 4:
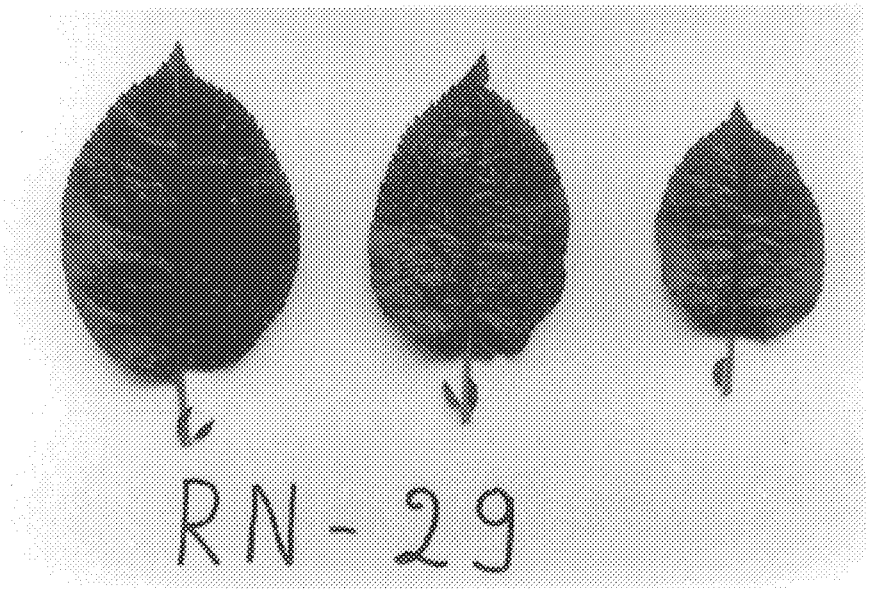
FIG. 4 shows the fine leaf serrations.
Figure 5:
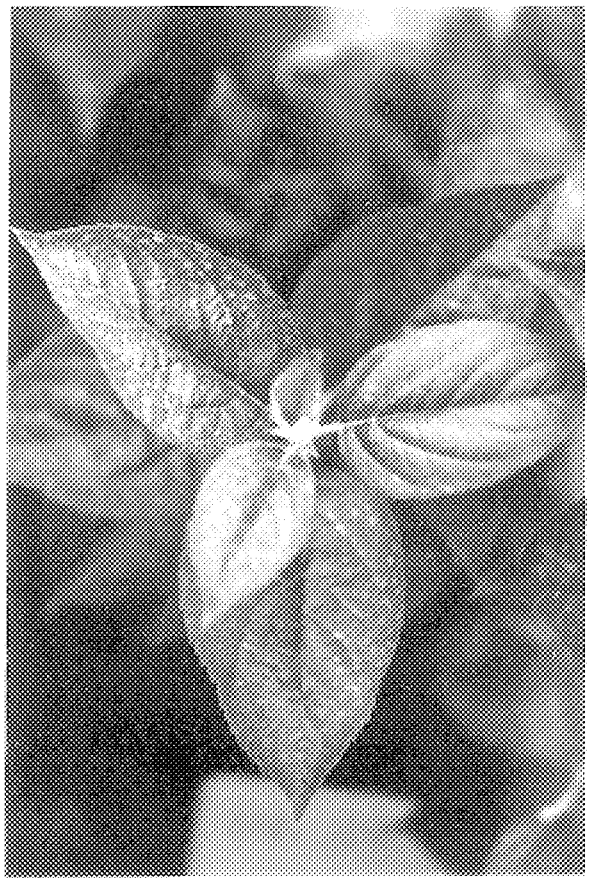
FIG. 5 shows the pink top growth of new shoots with the pale yellow-green color of older leaves.
Figure 6:
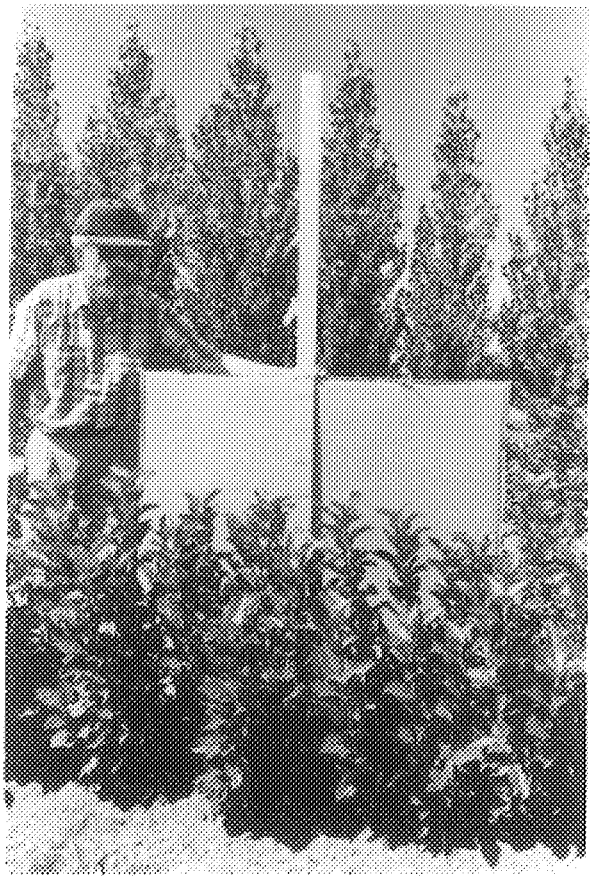
FIG. 6 shows the average height in centimeters of M9 rootstock daughter plants in a stoolbed row in Ephrata, Wash.
Figure 7:
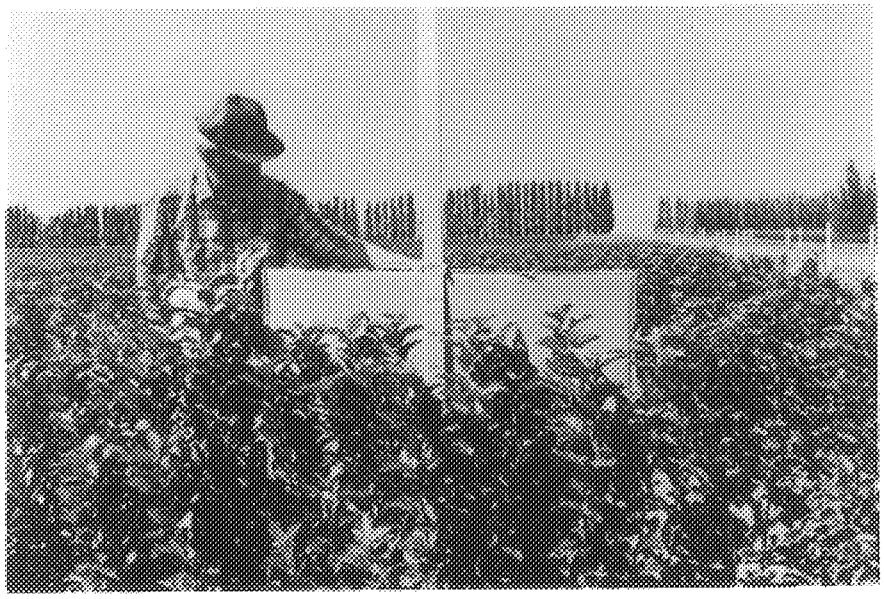
FIG. 7 shows the average height in centimeters of RN29 rootstock daughter plants in a stoolbed row in Ephrata, Wash.

The following is a detailed description of the new apple rootstocks growth characteristics based on the stoolbed plants grown at the six test sites described above. Colors of the leaves and shoots are based on their appearance at the sites where grown. In those instances where a precise color assessment can be made, reference is to the Munsell Limit Color Cascade Table. In other instances, general color terms are used in accordance with the ordinary dictionary significance.

General habit:
- *Strength of growth.*—Vigorous, stiff.
- *Habit.*—Upright.
- *Branching.*—Many, flexible, willowy.

Vegetative Shoots:
- *Bark color.*—Greenish-brown (22-14).
- *Pubescence.*—Finely tomentose.
- *Lenticels.*—Few, inconspicuous, widely spaced, small, yellow-white.

Leaves:
- *Size.*—Average, 5.7 cm wide, 8.6 cm long.
- *Shape.*—Broad elliptic, somewhat asymmetric, wavy.
- *Base.*—Obtuse, attenuated.
- *Apex.*—Mucronate.
- *Serrations.*—Finely serrate at sides, more obtuse margins at base.
- *Spacing.*—Normal phyllotaxical arrangement for Malus.
- *Color.*—Pale yellow-green (22-11) with pinkish tips.

Leaf scars:
- *Shape.*—Broad V, slightly raised.
- *Color.*—Dark brown.

Petioles:
- *Shape.*—Slender, slightly channeled.
- *Length.*—Medium, 2.85 cm.
- *Color.*—Reddish-brown (32-12).
- *Pose.*—Slight acute angle near tip, mostly horizontal.
- *Glands.*—None.

Stipules:
- *Size.*—Small, 3–5 mm, inconspicuous, some minutely serrated.
- Color.—Yellow-green.
- Pose.—Mostly reposed along petiole.

Lateral buds:
- *Size.*—Small.
- *Shape.*—Flat, angular.
- *Color.*—Dark brown.
- *Pubescence.*—Fine hairs, tomentose.

Apical buds:
- *Size.*—Larger than lateral buds.
- *Shape.*—Obtuse.
- *Color.*—Dark brown.
- *Pubescence.*—Tomentose.

Dormant Plant

Shoots:
- *Size.*—Stocky, 7.8–12.0 mm in caliper at base, stiff, brittle.
- *Bark color.*—Dark brown (25-15).
- *Pubescence.*—Conspicuously pubescent.
- *Nodes.*—Larger in diameter than internodes with shoulder at each side on leaf scar.
- *Internodes.*—Smooth, regularly spaced.

Stooling and Root Characteristics

Rooting and stooling: Multiplies well in stoolbeds, forming strong roots along full length of shank. Roots arise from nodes.

Flower Characteristics

Flowers:

*Size.*—3.5 cm in diameter.

*Color.*—White with pinkish streaks toward base.

Fruit (No commercial value but useful for identification):

*Shape.*—Round to slightly oblong. *Color.*—Red stripes. *Size.*—4.5 cm in diameter, 5.5 cm in length. *Flavor.*—Bland, tasteless.

General Characteristics

Rootsuckering: Slight.

Size control potential: Size of trees budded on the subject rootstocks will vary according to the vigor of the cultivar, condition and type of soil and orchard management. "Standard" growing cultivars such as Red and Golden Delicious are reduced in size about 65% when compared to trees on apple seedling rootstocks. Less vigorous varieties are more reduced in size and more vigorous varieties are less reduced in size.

Dwarfing: Fully dwarfing.

Precocity: Varies according to variety, most cultivars often flower and set fruit the first year in the orchard and thereafter bear fruit each year.

Compatibility: Graft compatible with all major commercial fruiting varieties.

Root anchorage: Needs support.

Hardiness: Hardy in most commercial apple growing areas.

Disease and pest resistance: Average resistance to common diseases and pests of apple. Tested and found free of all known virus and virus-like diseases to apple.

What is claimed is:

1. A new and distinct apple tree clone, a sport of the Malling 9, referred to by the cultivar designation 'M9-RN29', substantially as herein shown and described, characterized particularly by its ability to serve as a root-stock for grafting of apple tree cultivars to produce dwarf apple trees and by its ability to root very readily in the stoolbed and produce high quality stoolbed rootstock plants for nursery use.

* * * * *